United States Patent [19]
Bennewitz

[11] 3,987,676
[45] Oct. 26, 1976

[54] RELATIVE HUMIDITY DETECTOR

[76] Inventor: Paul F. Bennewitz, 623 Wyoming Blvd. SE., Albuquerque, N. Mex. 87123

[22] Filed: Nov. 28, 1975

[21] Appl. No.: 635,574

[52] U.S. Cl. .............................. 73/336.5; 204/38 A; 338/35
[51] Int. Cl.$^2$ ........................................ G01N 25/56
[58] Field of Search ............. 73/335, 336.5; 338/35; 324/61 P; 204/38 H, 38 S

[56] References Cited
UNITED STATES PATENTS

| | | | |
|---|---|---|---|
| 3,075,385 | 1/1963 | Stover | 73/335 |
| 3,121,853 | 2/1964 | Jason | 338/35 |
| 3,345,596 | 10/1967 | Delaney | 338/35 |
| 3,440,372 | 4/1969 | Cecil | 200/61.4 |
| 3,523,244 | 8/1970 | Goodman | 324/61 |
| 3,540,278 | 11/1970 | Diamond | 73/336.5 |
| 3,550,057 | 12/1970 | Young | 338/34 |
| 3,683,243 | 8/1972 | Rockliff | 317/246 |
| 3,861,031 | 1/1975 | Furuichi | 29/610 |

OTHER PUBLICATIONS

Storer, C. M., New Aluminum Oxide Humidity Element, (second report), Sandia Laboratories Publication SC-4667(RR), Mar. 1962.

Primary Examiner—S. Clement Swisher

[57] ABSTRACT

A relative humidity detector, is formed upon a substrate such as glass or amorphous quartz. An aluminum layer evaporated onto the substrate has a layer of $Al_2O_3$ anodized thereover to a thickness of 5,000 to 10,000 angstroms. A gold upper metallic layer overlies an adherent layer of chromium upon the $Al_2O_3$ to a combined thickness of 1000 Angstroms. After the substrate has been mounted onto an appropriate header, it is submerged in a water bath for about 8 to 12 hours. It is then heated at a temperature of about 120° C. for 6 to 12 hours. The submersion and heating process produces an impedance variation at 1000 Hz which is linear over the relative humidity range of between zero and 100%.

In another embodiment, an electrode of gold over chromium evaporated onto a portion of the substrate forms a first electrode. A layer of aluminum evaporated over the substrate and a portion of the first electrode has a layer of $Al_2O_3$ thereover. A layer of gold overlying an adherant layer of chromium is formed over a portion of the layer of $Al_2O_3$. A second electrode of gold and chrome overlies an edge portion of the top gold layer, and extends away from it onto the underlying substrate. Electrical connections are made to the first and second electrodes.

23 Claims, 6 Drawing Figures

RELATIVE HUMIDITY DETECTOR

BACKGROUND OF THE INVENTION

1. FIELD OF THE INVENTION

This invention relates to improvements in relative humidity detectors, and, more particularly, to an improved humidity detector for measuring relative humidity between zero and 100% by changes in its electrical impedance, and methods for making same.

2. DESCRIPTION OF THE PRIOR ART

Humidity sensors of the type which change resistance and/or capacitance have been proposed. Ordinarily, the sensors heretofore advanced employ a first layer of metal, a layer of hygroscopic material such as aluminum oxide or the like, and a second layer of metal, typically gold, formed over the aluminum oxide in the form of a sandwich. The second layer is ordinarily sufficiently thin to allow water molecules to pass therethrough to the hygroscopic layer, causing changes in the impedance between the first and second metallic layers.

In the humidity detectors heretofore used, although the response has been relatively good over the desired humidity range of interest, for instance, zero to 100%, it is ordinarily not precisely linear over the entire humidity range to be measured. Therefore, ordinarily, additional corrective elements must be used in association with the impedance measuring or detecting circuitry to correct for these variations.

Also, the devices heretofore advanced are of relatively large dimensions, and are not suitable for many microminiature circuit applications.

SUMMARY OF THE INVENTION

In light of the above, it is, therefore, an object of the invention to provide an improved humidity sensor.

It is another object of the invention to provide a humidity sensor of the type which exhibits an impedance which varies in direct relationship with variations in surrounding relative humidity.

It is another object of the invention to provide a method for making a humidity sensor.

It is another object of the invention to provide a method for making a humidity sensor having a linear impedance variation with variations in relative humidity from zero to 100%.

It is another object of the invention to provide a microminature humidity detector.

These and other objects, features and advantages will become apparent to those skilled in the art from the following detailed description when read in conjunction with the accompanying drawings and appended claims.

The humidity sensor, in accordance with the invention, exhibits an extremely precise linear impedance change with respect to changes in relative humidity, from zero to 100%. This response is produced in part by the physical dimensions of the device formed, and by the particular aging process by which it is treated.

More particularly, the humidity detector in accordance with the invention for measuring relative humidity includes a header upon which is mounted an appropriate substrate, such as amorphous quartz. In one embodiment, a layer of aluminum is deposited on the substrate to a thickness of between approximately 20,000 and 30,000 A. A layer of $Al_2O_3$ is formed on the aluminum by an anodizing process to a thickness of no more than 10,000 A. and no less than 5,000 A. A layer of metal is deposited on the layer of $Al_2O_3$, the metal being selected from the group consisting of gold, platinum, copper and silver. The layer is of thickness of about 1,500 A., permitting water molecules from the surrounding air to pass through the metal layer to the layer of $Al_2O_3$. A pair of electrodes are attached directly to the aluminum layer and the overlying metal layer.

In another embodiment, a first electrode is evaporated onto the substrate prior to the deposition of the aluminum layer, and a second electrode is evaporated onto the metal layer previously deposited over the $Al_2O_3$. Electrical connections are attached to the first and second electrodes at a point away from the detector.

In another aspect of the invention, means are provided in association with the metal-oxide-metal sandwich to compensate for variations in surrounding or ambient temperatures to provide an accurate indication of relative humidity over a wide temperature range.

In accordance with the method of the invention, the metal-oxide-metal structure is aged by submerging it in water followed by heating it at a temperature of about 120° C. for a time of between about 6 and 8 hours to produce a linear impedance response to changes in relative humidity between zero and 100%.

BRIEF DESCRIPTION OF THE DRAWING

The invention is illustrated in the accompanying drawing, wherein:

In FIGS. 1 and 6, the various sizes and dimensions of the parts have been exaggerated or distorted for clarity of illustration and ease of description.

DETAILED DESCRIPTION OF THE PREFERRED EMBODIMENTS

Figure 1:
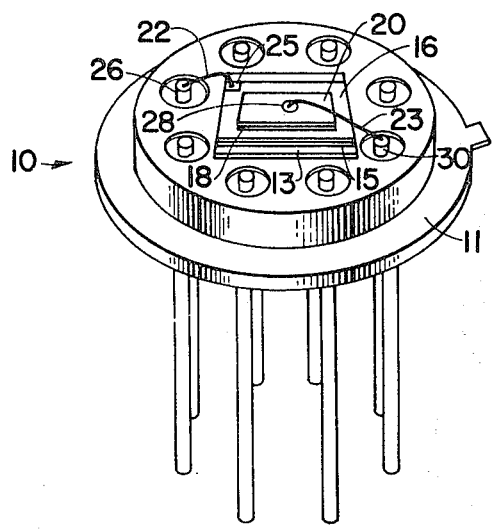
FIG. 1 is a perspective view of a humidity detector structure fabricated in accordance with the principles of the invention.

A humidity detector formed in accordance with the invention is shown in FIG. 1 and is illustrated generally by the reference numeral 10. The humidity detector 10 is formed on a standard 8 pin transistor header 11. The detector is formed upon a substrate 13 of glass, amorphous quartz or the like. The particular choice of the substrate used is not critical, but it should be of a material which is electrically insulating, and which has a relatively low temperature coefficient approximating that of the subsequent layers to be deposited thereon, as described below. It has been found that amorphous quartz is particularly well suited for such use.

A layer 15 of metal, such as aluminum, is formed on the substrate 13, having a thickness of about 10,000 to 20,000 A. A layer of hygroscopic material is formed on the layer 15 of thickness between 5,000 and 10,000 A. The layer 16 is conveniently of $Al_2O_3$ formed upon an aluminum base 15.

A metallic layer is formed on the hygroscopic layer 16, and is conveniently of gold. Thus, in the embodiment illustrated, a layer of chrome 18 is formed onto the hygroscopic layer 16, followed by a second layer 20 of gold. The layer 18 of chrome serves to bond or adhere the subsequently formed layer 20 of gold to the structure.

A pair of electrodes 22 and 23 are attached respectively to the lower metallic layer 15 and to the upper metallic layer 20. For example, the electrode or lead 22 is attached by electrically conducting glue directly to the metallic layer 15 in an area 25 from which the hygroscopic material has been scraped away or otherwise removed. The electrode 22 is bonded or otherwise attached to a terminal 26 for external connection.

The electrode or lead 23 is similarly attached by an electrically conducting glue at a junction 28 upon the gold layer 20, at one end, and to a terminal 30 at the other end for external connection.

The structure upon the substrate 13 is in the general form of a capacitor, having conducting plates formed by the metallic layers 15, 18 and 20, separated by a dielectric layer 16. The structure exhibits an impedance which varies with the relative humidity to which it is exposed, as discussed below further in detail.

The structure 10 of FIG. 1 serves as a humidity detector and may be useful in many applications. However, because of the use of the electrically conducting glue used to form the electrical connection between the leads 22 and 23 and the humidity detector, difficulty may be experienced in stabilizing the detector response, in many instances, due to the aging properties of the glue used.

Figure 2:
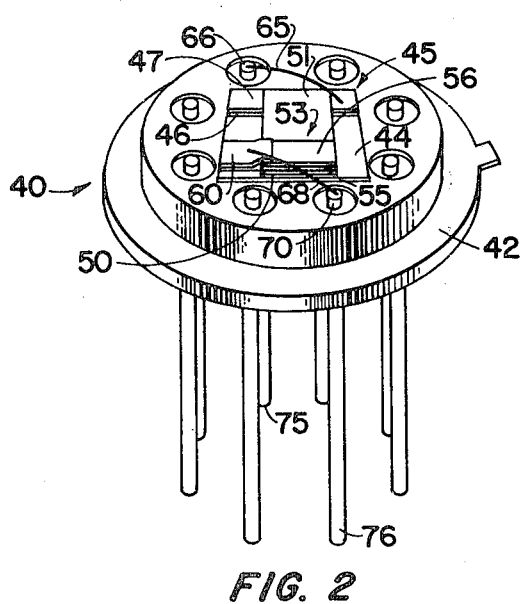
FIG. 2 is a perspective view of another embodiment of a humidity detector structure fabricated in accordance with the principles of the invention.

In those instances in which such response changes are objectionable, a structure fabricated in the form shown in the embodiment of FIG. 2 may be used. As shown, a humidity detector, generally denoted by the reference numeral 40, is fabricated upon a transistor header 42, in a fashion similar to the embodiment of FIG. 1. In the embodiment of FIG. 2, a substrate 44 of, for example, amorphous quartz or the like, is attached to the header 42. A first electrode 45 is formed on the substrate 44 by vapor deposition or similar technique. The electrode 45, covering only a portion of the substrate 44, is of a layer of chrome 46 over which a subsequent layer of gold 47 is deposited. The chrome, as is well known in the art, serves to adhere the gold to the underlying substrate.

A layer 50 of aluminum is deposited onto the substrate 44, overlying the gold layer 47 previously deposited. The layer of aluminum 50 is anodized to produce a layer of 51 of $Al_2O_3$ thereover.

A layer of metal 53 is deposited over a portion of the layer of $Al_2O_3$. The layer 53 includes an underlying layer 55 of chrome and an overlying layer 56 of gold. The layer 53 is of sufficient thinness to permit water molecules to pass therethrough to contact the underlying layer of $Al_2O_3$, as below described. A second electrode 60 is then deposited onto an edge portion of the layer 53, extending away therefrom onto the underlying substrate 44. The electrical contact 60 can be of gold.

Electrical connections are established to the first electrode 47 by a lead 65, which can be electrically bonded to the electrode 47 at one end and to a terminal connection 66 at the other. Likewise, a lead 68 can be electrically bonded to the second electrode 60 at one end, and to a terminal 70 at its other end. Therefore, electrical connection can be made to the humidity detector element by appropriate external connections (not shown) to the respective pins 75 and 76 connected to the terminals 66 and 70, respectively.

In the embodiment of FIG. 2, since all of the connections made to the various elements of the device are electrically bonded, no aging problems due to the connections are encountered.

The device of FIGS. 1 and 2 are formed in accordance with the method as presently described. The method is described with reference to the box flow diagram of FIG. 3. The method is described in particular terms of the embodiment of FIG. 2. It should be understood, however, that the same principles and techniques are equally applicable to the FIG. 1 embodiment.

The amorphous quartz substrate 44 is first prepared, box 80, for receiving the various layers to be evaporated onto it. The substrate first is cleaned in a solution of distilled water and detergent and exposed to ultrasonic waves. After this it is dipped into an alcohol solution, followed by another rinse in the ultrasonic bath. The substrate is then sputter etched in an argon atmosphere to remove the first few molecular layers thereof to provide a clean surface for receiving the subsequent metallic evaporation.

The substrate is then masked in accordance with well known vapor deposition masking techniques, and the first electrode 45 is evaporated thereonto, box 81. The electrode is formed by first evaporating the layer 46 of chromium, and subsequently evaporating the layer 47 of gold thereover. The chromium layer, as is well known in the art, forms a surface to which the subsequently deposited gold will adhere.

The substrate is then remasked, and the layer 50 of aluminum is evaporated onto the cleaned substrate 44, as depicted in the box 40 in FIG. 2. The aluminum extends only over a portion of the substrate 44, but extends at least over a portion of the first electrode 45. Thus, the layer 50 of aluminum is in electrical contact with the layer 47 of gold.

It should be pointed out here that the structures formed by successive vacuum atmosphere evaporation deposition techniques, as will become apparent, is particularly suited to production in quantities by well known masking techniques for the successive deposition steps. The details of the various masking steps are not described herein further in detail.

The layer 50 of aluminum is evaporated to a thickness of between approximately 20,000 and 30,000 A., the thickness being larger than that of the ultimately formed device, due to the subsequent anodizing of a portion thereof. The aluminum used is high purity, being at least 99.9% pure.

After the layer 50 aluminum has been deposited onto the substrate 13, it is anodized, box 83, to form a layer 51 of $Al_2O_3$ on the aluminum layer 50. The aluminum layer 50 is anodized by submerging it into a solution of sulphuric acid, 25% by volume, and exposing it to an A–C current, for a time sufficient to form a layer 51 of $Al_2O_3$ approximately 5,000 to 10,000 A. in thickness. The formation of the aluminum oxide from the material of the underlying preformed layer 50 will reduce the thickness of the aluminum layer 50 to between about 15,000 and 20,000 A., and, as stated, the layer of $Al_2O_3$ is between about 5,000 and 10,000 A. thick. A metallic layer 53 is then formed over the layer 51 of $Al_2O_3$, box 84. The layer 53 is of critical thickness, since the water molecules to be measured in the surrounding atmosphere must be able to pass through the metallic layer 53 to the underlying layer 51 of $Al_2O_3$. To achieve this thickness, the structure is then again placed in a vacuum atmosphere together with a monitor slide. The monitor slide within the vacuum chamber is visible to the operator, and functions to indicate the quantities of the subsequently deposited metals onto the substrate. First, chrome is deposited onto the layer 51 of the $Al_2O_3$ to form a layer 55 of approximately 400 to 500 A. The thickness of the chrome layer can be roughly determined by observing the monitor slide until it becomes discolored with the chrome, at which time the chrome deposition is discontinued. Then, gold is evaporated in the vacuum chamber to form a layer 56 of between about 400 to 500 A. The depth of the gold deposition onto the chrome can be estimated by observing the monitor slide, and, when it approaches opacity, the gold deposition is discontinued. The gold used in this step is 99.99% pure, and, again, the chrome onto which it is evaporated serves primarily as an adhesive to assure the gold layer 56 will adhere to the underlying oxide layer 51.

The second electrode 60 is then evaporated onto the structure, box 85. The second electrode 60, as shown in FIG. 2, is located principally in the substrate 44, but extends partially onto the layer 53 to establish electrical connection thereto. The thickness of the second electrode 60, as well as the thickness of the first electrode 45 is not critical, their primary function merely being to establish electrical connection to the layer 56 of gold and the layer 50 of aluminum, respectively. The second electrode 60 is also of gold deposited onto a chrome base, in the manner similar to that of the first electrode 45.

The structure thus formed is then cut into pieces (assuming that a large number of these structures have been formed by masking techniques, as above indicated) and each of the structures is mounted onto an appropriate header, box 87, in the fashion and manner shown in FIG. 2. The structure can be attached with an appropriate glue to the header 42, such as a glue sold under the trademark Kodak 310.

After the substrate 44 has been mounted to the header 42, the electrodes 65 and 68 are attached to the first bottom electrode 45 and second top electrode 60 by spot welding or other bonding technique.

Although the material of the first and second electrodes, 45 and 60 respectively, and the metal layer 53 have been described as being of gold, or gold over chrome, it should be pointed out that other metals can also be used. For example, it has been found that platinum can be used also. Other metals such as silver and copper also may be employed if desired.

Figure 4:
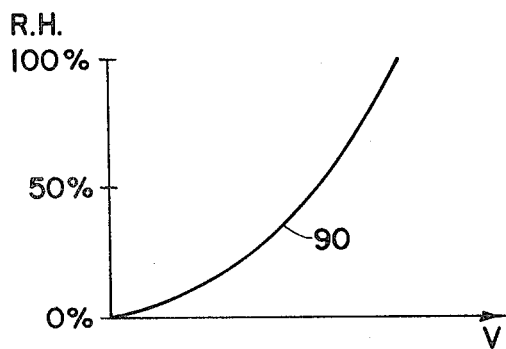
FIG. 4 is a graph of the impedance (shown as a voltage function) of the structure of FIG. 2 at 1,000 Hz versus relative humidity, prior to aging.

The structure thus formed functions as a humidity detector. Because of the relative thinness (approximately 1,000 A.) of the gold layer 56 and chrome layer 55, water molecules in the surrounding air are free to pass therethrough into the oxide layer 51. The water molecules have the effect of varying the impedance of the structure measured between the aluminum layer 50 and gold layer 56. A graph of a typical impedance variation with respect to variations in relative humidity from zero to 100% is shown in FIG. 4. (The graph shown in FIG. 4 is actually relative humidity versus the voltage developed across the humidity detector 40 when used in combination with the circuit of FIG. 6, below described. The voltage, however, represents the variation in the impedance of the detector 40, being proportional thereto assuming a constant voltage source.) From the graph, it can be seen that the impedance varies relatively linearly with changes in the relative humidity as shown by the line 90. However, over the range of humidities, a slight curve appears in the line, as shown.

It has been found that the curve shown can be almost completely linearized from zero to 100% if the structure of the humidity detector is aged, in the manner below described. First, the structure 40 is submerged in distilled water for a time period of between 8 to 12 hours, box 93. The water enters the various pores of the oxide layer, and tends to soften the layer somewhat.

The device is then removed from the distilled water and heated at a temperature of about 120° C. for a period of between about 6 to 12 hours, box 94. The heating temperature is higher than the boiling point of the water, and, consequently, dries the structure, purging the water which might be contained therewithin. The temperature, however, is less than the melting temperature of any of the components employed in the production of the system, and particularly that of the oxide layer. The heat consequently rehardens the oxide layer. Because of the initial softening and hardening process, any stresses which may have been set up in the intercrystalline lattice of the oxide are relieved. It has been found that the exposure to the temperature beyond 12 hours has no particular additional advantage in linearizing the impedance versus relative humidity curve.

Figure 3:
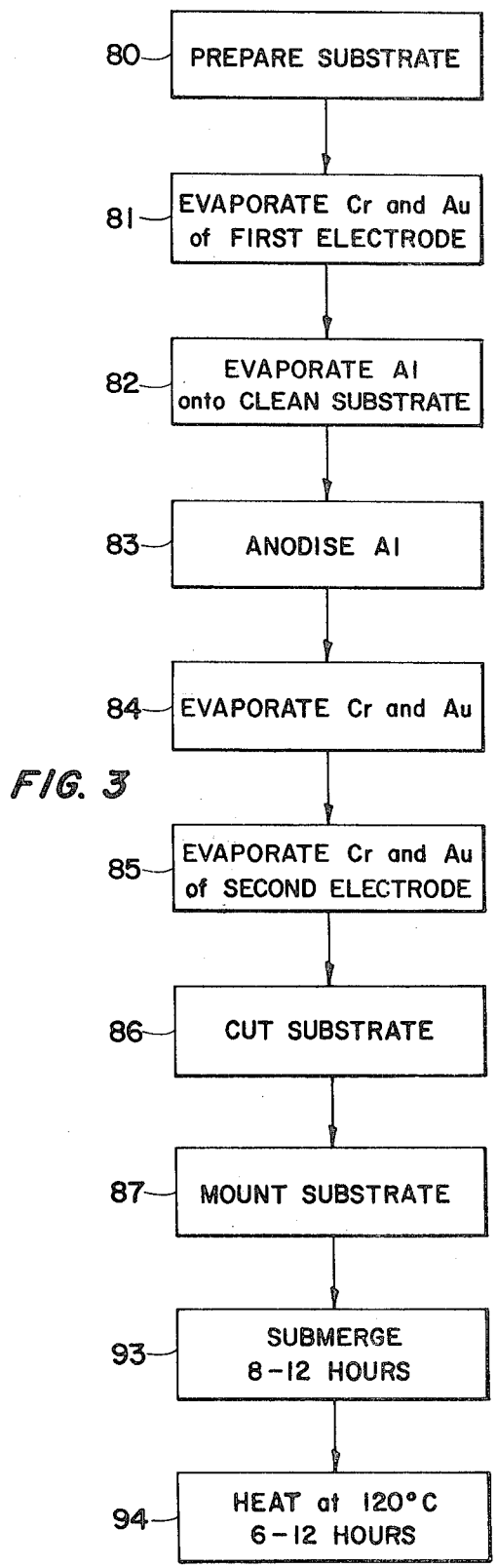
FIG. 3 is a block-flow chart illustrating the steps in fabricating the humidity detector device of FIG. 2.
Figure 5:
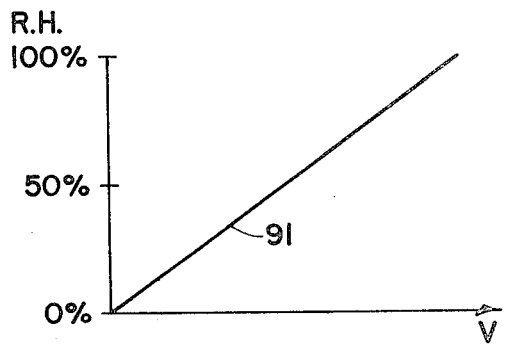
FIG. 5 is a graph of the impedance (shown as a voltage function) of the device of FIG. 1 at 1,000 Hz versus relative humidity, after aging.

The impedance versus relative humidity curve which is obtained after the aging and in accordance with the submersion and subsequent heating steps is shown in FIG. 5. Thus, as shown by the line 91, the impedance is entirely linear over the relative humidity range of zero to 100%. That is, the anomalous curve 90 over the relative humidity range as previously explained (FIG. 4) is removed, and the response is linear. Although not particularly apparent from the curves of FIG. 4 and FIG. 5, the curve of FIG. 5 is shifted slightly downwardly from the curve of FIG. 4. This shift has no effect insofar as the use of the humidity detector of the invention, but interestingly, is an indication of the completeness of the aging process effected by the submersion and heating steps 93 and 94 (FIG. 3). Thus, when the device is being aged, until aging is complete, further shifting of the curve 91 is apparent. After the completion of the aging, for example, at the completion of the 12 hours of the heating step (box 94) no further shift is apparent, regardless of the continued time of heating. Furthermore, if the properly aged device is recycled through the submersion and heating steps, boxes 93 and 94, there is no apparent shift in the curve 91, as seen in FIG. 5.

Figure 6:
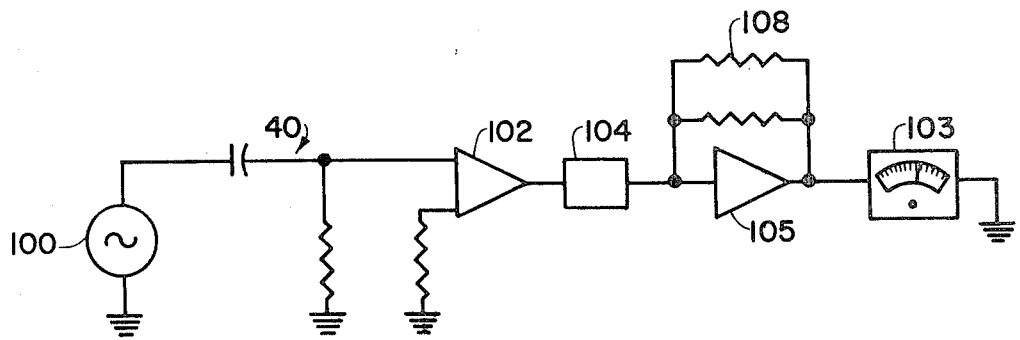
FIG. 6 is an electrical schematic diagram showing a circuit for incorporating the humidity detector of FIG. 1 for measuring relative humidity.

A circuit in which the humidity detector 40 can be employed is shown in FIG. 6. As seen, the humidity detector 40 is depicted as a capacitor, it being understood that the actual humidity detector of the invention exhibits both pure resistance and capacitive reactance. A constant voltage source of A–C signal, such as an A–C voltage source 100, or the like, is connected across the humidity detector 40. The frequency of the A-C source can conveniently be 1,000 Hz., that frequency being readily available in commercially available signal generators. The signal is conducted to an amplifier 102 which produces an output which is detected by a detector 104, measurable on a voltmeter 103 or other device for measuring the output of the amplifier 102. It has been found, for example, that a digital voltmeter is particularly convenient in monitoring the output of the amplifier 102, since, with appropriate scaling means, such as an amplifier 105, the relative humidity can be directly read. Thus, the input to the amplifier 102 from the signal generator 100 varies linearly with variations in relative humidity, in accordance with the curve 91 as shown in FIG. 5. The output, therefore, as read upon the meter 103 is a direct indication of the relative humidity.

Because relative humidity is defined in terms of the temperature at which it is measured, it is desirable to compensate for temperature variations in the vicinity of the humidity detector 40. (This temperature compensation does not involve the linearity of the impedance response, but only the location of the response curve.) For this purpose, a thermistor 108 is connected to the amplifier 105 to provide a feedback signal thereto. The thermistor 108 varies the output of the amplifier 105 depending upon the temperature in the vicinity of the humidity detector 40. Ideally, because of the plurality of pins which are available on a typically used header, such as the 8 pin header 42 shown in FIG. 6, the thermistor 108 can easily be mounted between two unused pins of the header 11. It will be, therefore, in the immediate vicinity of the humidity detector structure, and, therefore, can be connected to compensate for temperature variations in the vicinity of the detector structure 40.

Although the invention has been described and illustrated with a certain degree of particularity, it is understood that the present disclosure has been made only by way of example, and that numerous changes in the combination and arrangement of parts may be resorted to without departing from the spirit and scope of the invention as hereinafter claimed.

I claim:
1. A method for making a humidity detector, comprising:
   forming successive layers of a first electrical conductor, a hygroscopic material consisting essentially of $Al_2O_3$, and a second electrical conductor upon a substrate, whereby the electrical impedance between said first and second electrical conductors varies with variations in humidity,
   submerging said successive layers into water, and subsequently exposing said successive layers to a temperature of about 120° C., whereby said impedance variation is made essentially linear for variations in relative humidity between 0% and 100%.
2. The method of claim 1 wherein said submerging is for a time of about 12 hours.
3. The method of claim 1 wherein said heating comprises exposing said successive layers to said temperature for a time of between approximately 6 and 12 hours.
4. The method of claim 1 wherein said forming successive layers comprises:
   evaporating a layer of aluminum onto an amorphous quartz substrate,
   anodizing said aluminum layer to form said layer of $Al_2O_3$, and,
   evaporating a layer of chrome and a layer of gold onto said layer of $Al_2O_3$.
5. The method of claim 4 wherein said first layer of aluminum is of thickness of between approximately 15,000 and 20,000 A., said layer of $Al_2O_3$ is of thickness of between approximately 5,000 and 10,000 A., and said third layer of chrome and gold is of thickness of about 1,500 A.
6. The method of claim 1 wherein said step for forming said second electrical conductor comprises providing a material selected from the group consisting of gold, silver, copper and platinum.
7. A method for making a humidity detector, comprising:
   evaporating an aluminum layer onto a substrate to a depth of between approximately 20,000 and 30,000 A.;
   forming a layer of $Al_2O_3$ upon said substrate of thickness between 5,000 and 10,000 A.;
   evaporating chrome onto said layer of $Al_2O_3$ to a depth of about 700 A.;
   evaporating gold onto said layer of chrome to a depth of approximately 800 A.;
   submerging the aforesaid layers into water for about 12 hours;
   and heating the aforesaid layers at a temperature less than the melting temperature of said $Al_2O_3$ to evaporate said water therein and to relieve any intercrystalline stresses therein to produce a linear impedance relationship to humidity of said structure.
8. The method of claim 7 wherein said heating comprises exposing the aforesaid layers to a temperature of approximately 120° C. for a time of between approximately 6 and 12 hours.
9. A humidity detector made in accordance with the method of claim 7.
10. A humidity detector made in accordance with the method of claim 1.
11. A method of linearizing the impedance response of a humidity detector of the type in which successive layers of aluminum, $Al_2O_3$, and gold are formed on a substrate, comprising:
   submerging said detector into a bath of water,
   removing said detector from said bath,
   and exposing said detector to a temperature of approximately 120° C. for a time sufficient to remove all of the water from said bath therein, and to relieve the intercrystalline stresses thereof.
12. The method of claim 11 wherein said heating step comprises heating said detector for a time of between approximately 6 and 12 hours.
13. A detector for measuring relative humidity comprising:
   a header,
   a substrate, mounted on said header,
   a layer of aluminum on said substrate of thickness of between approximately 10,000 and 20,000 A., a layer of $Al_2O_3$ of thickness no more than 10,000 A., and no less than 5,000 A. on said layer of aluminum,
   a layer of metal formed on said layer of $Al_2O_3$, said metal layer being selected from the group consisting of gold, platinum, copper and silver, said metal layer being of thickness of about 1,500 A., whereby water molecules from the surrounding air can pass through said metal layer and to said layer of $Al_2O_3$, and a pair of electrodes connected directly to said layer of aluminum and said metal layer, respectively, whereby the impedance of said structure varies linearly with variations in the relative humidity between 0% and 100%.

14. The humidity detector of claim 13 wherein said metal layer is gold.

15. The humidity detector of claim 13 wherein said metal layer is platinum.

16. The humidity detector of claim 13 wherein said aluminum layer, said $Al_2O_3$ layer, and said metal layer are free of intercrystalline stresses.

17. The humidity detector of claim 13 wherein said aluminum layer is of dimensions approximately ⅛ inch square.

18. The humidity detector of claim 13 further comprising:
an alternating signal generator connected across said metal layer and said aluminum layer,
an amplifier connected to receive the signal of said signal generator, and,
a thermistor in proximity to said humidity detector connected to said signal generator to vary the gain thereof with variations in temperature, whereby the magnitude of the signal output of said amplifier indicates the impedance of said structure.

19. The humidity detector of claim 18 wherein said signal of said signal generator is of frequency of approximately 1,000 Hz.

20. The humidity detector of claim 14 further comprising an layer of chromium between said layer of $Al_2O_3$ and said layer of gold of thickness of approximately 200 to 500 A.

21. A detector for measuring relative humidity comprising:
a header,
a substrate mounted on said header,
a first electrode evaporated onto a portion of said substrate,
a layer of aluminum on a portion of said substrate, overlying at least a portion of said first electrode, said layer of aluminum being of thickness between approximately 10,000 and 20,000 A.,
a layer of $Al_1O_3$ of thickness of no more than 10,000 A. on said layer of aluminum,
a layer of metal formed on said layer of $Al_2O_3$, said metal layer being selected from the group consisting of gold, platinum, copper and silver, said metal layer being of thickness of about 1,500 A., whereby water molecules from the surrounding air can pass through said metal layer and to said layer of $Al_2O_3$,
a second electrode on said substrate, in contact with said layer of metal formed on said layer of $Al_2O_3$,
and a pair of electrodes bonded to said first and second electrodes, respectively,
whereby the impedance of said structure measured upon said electrodes varies linearly with variations in the relative humidity between zero and 100%.

22. The humidity detector of claim 20 wherein said metal layer is gold.

23. The humidity detector of claim 20 wherein said aluminum layer, said $Al_2O_3$ layer and said metal layer are free of intercrystalline stresses.

* * * * *